United States Patent [19]

Grosselin

[11] Patent Number: 5,097,064

[45] Date of Patent: Mar. 17, 1992

[54] PROCESS FOR PREPARING OPTICALLY ACTIVE 2-ARYLPROPIONIC ACIDS

[75] Inventor: Jean-Michel Grosselin, Lyons, France

[73] Assignee: Rhone-Poulenc Sante, Antony, France

[21] Appl. No.: 575,398

[22] Filed: Aug. 30, 1990

[30] Foreign Application Priority Data

Sep. 5, 1989 [FR] France .................. 89 11568

[51] Int. Cl.$^5$ .......................................... C07B 57/00
[52] U.S. Cl. .................................. 562/401; 548/217; 548/444; 548/572; 549/58; 562/460; 562/461; 562/462
[58] Field of Search .............. 562/460, 461, 401, 462; 548/217, 444, 572; 549/58

[56] References Cited

U.S. PATENT DOCUMENTS

| | | | |
|---|---|---|---|
| 4,201,870 | 5/1980 | Zupancic ........................... | 562/460 |
| 4,279,926 | 7/1981 | Bruzzese et al. ............... | 562/462 X |
| 4,337,353 | 6/1982 | Allais et al. ..................... | 562/460 |
| 4,865,770 | 9/1989 | Piselli ............................... | 562/402 |
| 4,868,214 | 9/1989 | Sunshine et al. ................ | 514/568 |
| 4,946,997 | 8/1990 | Larsen et al. .................... | 562/401 |
| 4,970,336 | 11/1990 | Yoshioka et al. ................ | 562/460 |

FOREIGN PATENT DOCUMENTS

2021583 12/1979 United Kingdom .

OTHER PUBLICATIONS

*Chemical Abstracts*, vol. 112, No. 11:98158m, (1990), abstracting.
*Gazz, Chim, Ital.*, vol. 119, No. 4, pp. 229–233, (1989).
*Chemical Abstracts*, vol. 105, (1986), No. 24599q.
*Gazzetta Chimica Italiana*, vol. 110, No. 2,3, (Feb.–Mar. 1980), pp. 123–127.
*Chemical Abstracts*, vol. 110, No. 9, (Feb. 27, 1989), No. 75662r.

*Primary Examiner*—Jose G. Dees
*Assistant Examiner*—Vera C. Clarke
*Attorney, Agent, or Firm*—Morgan & Finnegan

[57] ABSTRACT

This invention relates to a process for preparing an optically active 2-arylpropionic acid of general formula (I), by the hydrogenation, in a heterogeneous aqueous-organic medium, of a 2-arylacrylic acid of general formula (II) in the presence of a catalyst consisting of a rhodium derivative and a water-soluble chiral ligand.

In the general formulae (I) and (II), Ar represents an optionally substituted monocyclic or polycyclic aromatic radical or an optionally substituted aromatic heterocyclic radical:

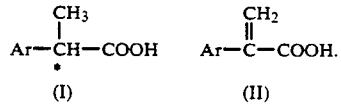

14 Claims, No Drawings

PROCESS FOR PREPARING OPTICALLY ACTIVE 2-ARYLPROPIONIC ACIDS

FIELD OF THE INVENTION

The present invention relates to a process for preparing optically active 2-arylpropionic acids of general formula:

by the asymmetric reduction of a 2-arylacrylic acid of general formula:

In the general formulae (I) and (II), Ar represents an optionally substituted monocyclic or polycyclic aromatic radical or an optionally substituted aromatic heterocyclic radical.

More especially, the present invention relates to the preparation of the S enantiomers of 2-arylpropionic acids which possess anti-inflammatory, analgesic and/or antipyretic properties.

Among therapeutically active 2-arylpropionic acids, there may be mentioned, e.g., ketoprofen-2-(3-benzoylphenyl)propionic acid, naproxen-d-2-(6-methoxy-2-naphtyl)propionic acid, ibuprofen-2-(4-isobutylphenyl)-propionic acid, suprofen-p-(2-thenoyl)hydratropic acid, fenoprofen-2-(3-phenoxyphenyl)propionic acid, benoxaprofen-2-(4-chlorophenyl)-α-methyl-5-benzoxazola-cetic acid, carprofen-6-chloro-α-methyl-9H-carbazole-2-acetic acid, cicloprofen, pirprofen-3-chloro-4-(3-pyrrolin-1-yl)hydratropic acid, flurbiprofen and fluprofen-2-(2-fluoro-4-biphenylyl)propionic acid.

Still more especially, the present invention relates to the preparation of the S-(+)enantiomer of 2-(3-benzoylphenyl)propionic acid [or (S)-(+)-ketoprofen].

BACKGROUND OF THE INVENTION

In U.S. Pat. No. 3,641,127, the synthesis has been described of (S)-(+)-ketoprofen by a process which requires a large number of successive stages to be carried out, and which, as a result, is difficult to apply on an industrial scale.

It is known, from G. Comisso et al., Gazzetta Chimica Italiana, 110, 123-127 (1980), to reduce 2-(3-benzoylphenyl)acrylic acid enantioselectively with hydrogen in the presence of a rhodium-based catalyst combined with a chiral ligand [(−)-DIOP], working in a homogeneous organic medium. However, the implementation of this process permits only a product whose optical purity is unsatisfactory to be obtained. Moreover, this process does not permit a recycling of the catalyst, thereby decreasing the economic value of the process.

DESCRIPTION OF THE INVENTION

It has now been found, and this forms the subject of the present invention, that the optically active 2-arylpropionic acids of general formula (I) may be obtained in good yield and with satisfactory enantiomeric excesses by the asymmetric reduction in a two-phase medium of a 2-arylacrylic acid of general formula (II).

According to the present invention, the asymmetric reduction of a 2-arylacrylic acid of general formula (II) is performed with hydrogen in the presence of a catalyst consisting of a rhodium derivative combined with a water-soluble chiral ligand, working in a two-phase aqueous-organic medium.

The rhodium derivatives which are especially well suited to carrying out the process are selected from the inorganic or organic salts and the complexes of rhodium such as, e.g., $RhCl_3$, $RhBr_3$, $Rh_2O$, $Rh_2O_3$, $Rh(NO_3)$, $Rh(CH_3COO)_3$, $Rh(CH_3COCHCOCH_3)_3$ and $[RhCl(1,5-cyclooctadiene)]_2$. Of very special importance are $[RhCl(1,5-cyclooctadiene)]_2$ and $RhCl_3$.

The water-soluble chiral ligands are selected from the sulphonated chiral phosphines which are described, in particular, in French Patent FR 83/12,468 (2,549,840). Preferably, tetrasulphonated (−)-cyclobutaneDIOP of formula:

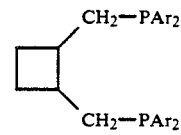

in which Ar represents the radical of formula:

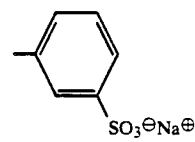

is used.

A quantity of rhodium or of rhodium compound is used, such that the number of gram-atoms of elemental rhodium per liter of reaction solution is between $10^{-4}$ and 1. Preferably, it is between 0.001 and 0.5.

For satisfactory implementation of the process, the quantity of phosphine is selected in such a way that the mole ratio of the ligand to the rhodium compound is between 1 and 100. Preferably, the ratio is in the region of 3.

According to a particular but non-mandatory embodiment of the process, a base may be added to the reaction mixture with the object of increasing the selectivity. Bases which are especially well suited are selected from alkali metal or alkaline earth metal hydroxides, carbonates or bicarbonates and tertiary aliphatic amines (triethylamine) or aromatic amines. The quantity of base is selected in such a way that the mole ratio of the base to the rhodium compound is between 1 and 100.

In general, the implementation of the process is accomplished by the hydrogenation by means of hydrogen, optionally under pressure, of a reaction mixture obtained by adding the catalytic aqueous solution to a solution of the 2-arylacrylic acid of general formula (II) in a non-water-miscible organic solvent preferably selected from esters such as ethyl acetate. When the hydrogenation is complete, the catalytic aqueous solution is separated after settling has taken place, the reaction product being in the organic phase, from which it may be separated, e.g. by evaporation of the solvent.

In general, the hydrogenation is performed under a hydrogen pressure of between 1 and 100 bars, and preferably in the region of 20 bars, at a temperature of between −50° and +100° C., and preferably in the region of 20° C.

The catalytic aqueous solution which is separated at the end of the reaction may be recycled into a subsequent hydrogenation operation.

The present invention also relates to the optically active 2-arylpropionic acids, and more especially to (S)-(+)-ketoprofen, when they are obtained by carrying out the process.

EXAMPLES

The examples which follow, given without implied limitation, illustrate the implementation of the process.

EXAMPLE 1

Tetrasulphonated (−)-cyclobutaneDIOP (0.060 g) and deaerated water (5 cc) are introduced under an argon atmosphere into a Schlenk tube. A solution (1 cc) of $[RhCl(1,5\text{-cyclooctadiene})]_2$ in a methanol/toluene mixture (1:1 by volume), equivalent to $1.3 \times 10^{-5}$ gram-atom of rhodium, is added. The mole ratio of the ligand to rhodium is 3. After 15 minutes' stirring at a temperature in the region of 20° C., the yellow catalytic aqueous solution is transferred to a 25-$cm^3$ glass flask containing 2-(3-benzoylphenyl)acrylic acid (0.001 mole) dissolved in ethyl acetate (5 cc). The flask is placed in a 125-cc autoclave. A hydrogen pressure of 20 bars is established. Hydrogenation is continued for 17 hours at a temperature in the region of 20° C.

When the hydrogenation is complete, the aqueous and organic phases are separated after settling has taken place. The aqueous phase is washed with ethyl acetate (3×100 cc). The combined organic phases are dried over sodium sulphate. After filtration and evaporation of the solvent, a yellow oil is obtained in a quantitative yield, the proton nuclear magnetic resonance spectrum of which oil shows that the degree of conversion of 2-(3-benzoylphenyl)acrylic acid is 100%;

analysis of which oil by chiral high performance liquid chromatography (chiral HPLC) shows that the enantiomeric excess of (S)-(+)-2-(3-benzoylphenyl)propionic acid is 71% (S/R=85:14).

2-(3-Benzoylphenyl)acrylic acid may be prepared according to the method described by G. Comisso et al., Gazzetta Chimica Italiana, 110, 123–127 (1980).

Tetrasulphonated (−)-cyclobutaneDIOP may be prepared according to the method described in French Patent FR 83/12,468 (2,549,840).

EXAMPLE 2

The procedure is as in Example 1, working in the presence of a quantity of triethylamine such that the triethylamine/rhodium compound mole ratio is equal to 5.6.

Analysis of the product obtained shows that the degree of conversion of 2-(3-benzoylphenyl)acrylic acid is 100%, and that the enantiomeric excess of (S)-(+)-2-(3-benzoylphenyl)propionic acid is 76% (S/R=88:12).

The present invention also relates to antiinflammatory, analgesic and/or antipyretic pharmaceutical compositions containing an optically active 2-arylpropionic acid of general formula (I), and more especially (S)-(+)-ketoprofen, obtained by carrying out the process, optionally in the form of a pharmaceutically acceptable salt, optionally in combination with one or more pharmaceutically acceptable adjuvants or diluents, either inert or pharmacologically active.

The pharmaceutically acceptable salts are generally selected from salts with inorganic or organic bases. As pharmaceutically acceptable salts, the salts of alkali metals or alkaline earth metals (sodium, potassium, calcium), the salts of heavy metals (copper, zinc), the salts of amines (triethylamine, triethanolamine) or the salts of amino acids (lysine, arginine) may be mentioned.

The pharmaceutical compositions according to the invention can be solid, liquid or semi-liquid compositions, which can be administered orally, parenterally or rectally or be used in local or ophthalmic applications.

As solid compositions for oral administration, there may be mentioned tablets, powders or granules which permit an immediate or controlled release of the optically active 2-arylpropionic acid of general formula (II).

As liquid compositions for oral administration, solutions, suspensions and emulsions, aqueous or non-aqueous, may be mentioned.

As liquid compositions for parenteral administration, aqueous or non-aqueous sterile solutions of an optically active 2-arylpropionic acid of general formula (I), optionally in salt form, may be mentioned.

As compositions for rectal administration, suppositories or gels may be mentioned.

As compositions for local application, salves, ointments, gels or transdermal forms may be used.

As compositions for ophthalmic application, eye lotions may be mentioned.

In human therapy, the doses depend on the administration route, the treatment period and the nature of the complaint to be treated. In general, the daily dosages are between 20 and 500 mg, in one or more doses.

The examples which follow, given without implied limitation, illustrate compositions according to the invention.

EXAMPLE A

Tablets containing (S)-(+)-ketoprofen (25 mg) and having the following composition are prepared according to the usual technique:

| | |
|---|---|
| (S)-(+)-ketoprofen | 25 mg |
| starch | 120 mg |
| precipitated silica | 27 mg |
| magnesium stearate | 3 mg |

EXAMPLE B

An injectable solution containing the following is prepared according to the usual techniques:

| | |
|---|---|
| (S)-(+)-ketoprofen | 25 mg |
| arginine | 18.3 mg |
| citric acid q.s. pH 6.5 | |
| injectable solution | 2 cc |

EXAMPLE C

A gel containing the following is prepared according to the usual techniques:

| | |
|---|---|
| (S)-(+)-ketoprofen | 0.75 g |
| gelling agent | 0.9 g |

-continued

| neutralizing agent | 1.8 g |
| --- | --- |
| ethyl alcohol | 8.1 g |
| distilled water q.s. | 30 g |

I claim:

1. A process for preparing an optically active 2-arylpropionic acid of the formula:

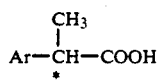

in which Ar represents a phenyl radical substituted by 3-benzoyl, 4-isobutyl, 3-phenoxy, (2-fluoro-4-phenyl), (4-(2,5-dihydro 1H-pyrrolyl)-3-chloro) or 2-thenoyl, a 2-(6-methoxynaphthyl) radical, a 5-(2-(4-chlorophenyl)-benzoxazolyl radical or a 2-(6-chloro 9H-carbazolyl) radical, by the reduction by means of hydrogen of a 2-arylacrylic acid of the formula:

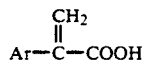

in which Ar is defined as above comprising performing the reaction in a two-phase aqueous-organic medium in the presence of a catalyst consisting of a rhodium derivative combined with a water-soluble chiral ligand.

2. The process according to claim 1, wherein the rhodium derivative is selected from the group consisting of an inorganic or organic salt and a complex of rhodium.

3. The process according to claim 2, wherein the rhodium derivative is selected from the group consisting of [RhCl(1,5-cyclooctadiene)]$_2$ and RhCl$_3$.

4. The process according to claim 1, wherein the water-soluble chiral ligand is a sulphonated chiral phosphine.

5. The process according to claim 4, wherein the water-soluble chiral ligand is tetrasulphonated (−)-cyclobutaneDIOP.

6. The process according to claim 1, 2 or 3 wherein a quantity of rhodium is used, such that the number of gram-atoms of elemental rhodium per liter of reaction solution is between $10^{-4}$ and 1.

7. The process according to claim 1, 2 or 3 wherein the mole ratio of the ligand to the rhodium compound is between 1 and 100.

8. The process according to claim 1, 2 or 3 wherein the reaction is performed under a hydrogen pressure of between 1 and 100 bars.

9. The process according to claim 1, 2 or 3 wherein the reaction is performed at a temperature of between $-50°$ and $+100°$ C.

10. The process according to claim 1, 2 or 3 wherein the reaction is performed, in addition, in the presence of an inorganic or organic base.

11. The process according to claim 10, wherein the base is triethylamine.

12. The process according to claim 1, 2 or 3 for the preparation of (S)-(+)-2-(3-benzoylphenyl)-propionic acid by the reduction of 2-(3-benzoylphenyl)-acrylic acid.

13. The process according to claim 1, wherein Ar is a 3-benzoylphenyl radical.

14. The process according to claim 1, wherein the rhodium derivative is selected from the group consisting of RhCl$_3$, RhBr$_3$, Rh$_2$O, Rh$_2$O$_3$, Rh(NO$_3$), Rh(CH$_3$COO)$_3$, RhCCH$_3$(OCHCOCH$_3$)$_3$ and (RhCl(1,5-cyclooctadiene))$_2$.

* * * * *